United States Patent [19]

Fancher

[11] 4,094,974
[45] June 13, 1978

[54] ISOXAZOLE PHOSPHATES AND PHOSPHONATES

[75] Inventor: Llewellyn W. Fancher, Orinda, Calif.

[73] Assignee: Stauffer Chemical Company, Westport, Conn.

[21] Appl. No.: 771,716

[22] Filed: Feb. 24, 1977

[51] Int. Cl.² .................... C07D 261/14; A01N 9/36
[52] U.S. Cl. ................. 424/200; 260/307 H
[58] Field of Search ..................... 260/307 H; 424/200

[56] References Cited

U.S. PATENT DOCUMENTS

| | | | |
|---|---|---|---|
| 3,562,288 | 2/1971 | Scherer et al. | 260/307 |
| 3,591,600 | 7/1971 | Fancher | 260/306.8 R |
| 3,700,771 | 10/1972 | Fancher | 424/200 |
| 3,755,571 | 8/1973 | Gaughan | 424/200 |
| 3,759,941 | 9/1973 | Sampei et al. | 260/307 H |
| 3,907,938 | 9/1975 | Stolzer et al. | 260/943 |

*Primary Examiner*—Raymond V. Rush
*Attorney, Agent, or Firm*—M. Henry Heines

[57] ABSTRACT

Insecticidally active compounds are disclosed, defined by the general formula

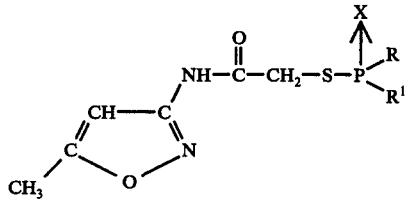

in which
R is alkyl or alkoxy each having 1 to 6 carbon atoms;
$R^1$ is alkoxy having 1 to 6 carbon atoms; and
X is oxygen or sulfur.

24 Claims, No Drawings

ISOXAZOLE PHOSPHATES AND PHOSPHONATES

BRIEF DESCRIPTION OF THE INVENTION

The present invention relates to a novel class of isoxazole compounds and to their use as insecticides when used in an insecticidally effective amount. In particular, this invention relates to compounds having the formula

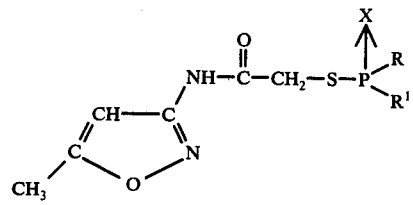

in which

R is alkyl or alkoxy each having 1 to 6 carbon atoms; preferably 1 to 5, 1 to 4, 1 to 3, or 1 to 2 carbon atoms; more preferably 2 to 5, 2 to 4, or 2 to 3 carbon atoms; with alkyl having 1 to 3, or 2 to 3 carbon atoms particularly preferred; and ethyl most preferred;

$R^1$ is alkoxy having 1 to 6 carbon atoms; preferably 1 to 5, 1 to 4, 2 to 4, or 2 to 3; more preferably ethoxy or branched-chain propoxy or butoxy; and X is oxygen or sulfur, preferably sulfur.

By "alkyl" is meant a straight- or branched-chain saturated hydrocarbon group containing the indicated number of carbon atoms. Examples of groups conforming to this description are methyl, ethyl, n-propyl, isopropyl, butyl, isobutyl, and sec-butyl.

By "alkoxy" is meant a straight- or branched-chain saturated hydrocarbonoxy group containing the indicated number of carbon atoms. Examples of groups conforming to this description are methoxy, ethoxy, n-propoxy, isopropoxy, butoxy, isobutoxy, and sec-butoxy.

All stated ranges of quantities of carbon atoms are intended to be inclusive of their upper and lower limits.

By "insecticidally effective amount" is meant the amount of the herein disclosed insectidical compounds which when applied in any conventional manner to the habitat of insects, the feedstuffs of insects, or the insects themselves, will kill or substantially injure a significant portion thereof.

DETAILED DESCRIPTION OF THE INVENTION

The compounds of this invention are prepared by the generalized reaction scheme shown below:

A. Chloroacetylation

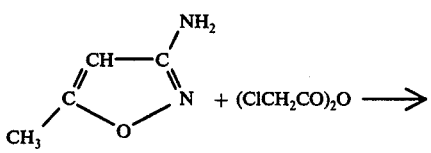

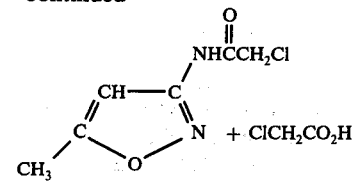

B. Condensation

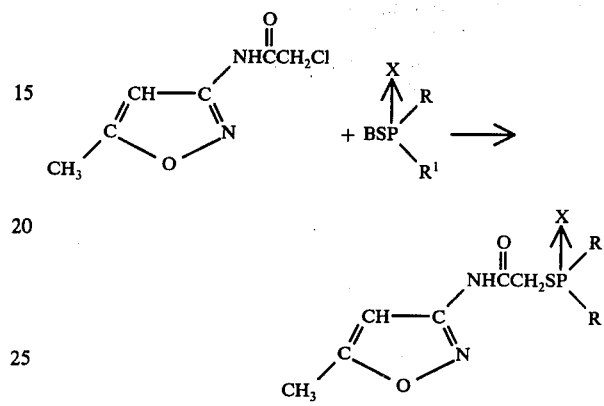

The groups R, $R^1$, and X are as defined above, and B is a base. Any base which forms a phosphorothiolate salt soluble in the reaction medium of Step B will be suitable. Examples of suitable bases are sodium, potassium, ammonium, and triethylamine. The phosphorothiolate salt can either be prepared prior to addition to the reaction mixture or generated in situ by neutralization of the appropriate phosphonodithioic acid with the basic material, particularly when the latter is an amine.

The starting materials are known and commercially available. The reactions are preferably run in the presence of organic solvents. Any polar or non-polar organic solvent which is inert to the system components and which will dissolve all reactants and products will be suitable. Examples of such solvents are dioxane, tetrahydrofuran, benzene, and dimethylformamide. Dimethylformamide is a preferred solvent for the condensation reaction since at low temperatures this reaction proceeds more readily with this solvent.

The above reactions will proceed at any temperature. Side reactions become more prominent as the temperature increases, however, raising the level of impurities in the final product. For this reason, it is preferred to run the reactions at approximately ambient temperature.

The following examples serve to illustrate the preparation of the compounds of the invention.

EXAMPLE I

3-O,O-Diethylphosphorodithioylacetamido-5-methyl isoxazole

To a solution of 19.6 parts by weight of 3-amino-5-methyl isoxazole in dioxane was added 43 parts by weight of chloroacetic anhydride. The addition was made in portions to maintain the temperature below 60° C. The mixture was then held at 60°–65° C for 15 minutes and let stand at ambient temperature for 30 minutes. The mixture was then poured into water and diluted with crushed ice. The solid was filtered off, washed with ice water and ether, then dried in an oven at 40° C, to produce 27.3 parts by weight (78.2% yield) of 3-chloroacetylamino-5-methyl isoxazole, melting point 188°–192° C with decomposition.

A dimethylformamide solution was made of 3.4 parts by weight of the above compound. To this solution was added 5.6 parts by weight of O,O-diethylphosphorodithioic acid, followed by the addition with cooling below 45° C of 3.0 parts by weight of triethylamine. The mixture was stirred for three hours at ambient temperature. The mixture was then diluted with benzene, washed with aqueous NaCl, dried over anhydrous MgSO$_4$ and filtered. The solvent retained in the solid was evaporated under vacuum. The solid was then slurried in hexane, filtered, and dried at 40° C to give 4.67 parts by weight (72% yield) of the title compound, structure confirmed by nuclear magnetic resonance (NMR) analysis, with melting point 103°–108° C.

EXAMPLE II

3-Ethyl-O-isopropylphosphonodithioylacetamido-5-methyl isoxazole

A dimethylformamide solution of 3.4 parts by weight of 3-chloroacetylamino-5-methyl isoxazole, see Example I above, was prepared. To this solution was added 5.5 parts by weight of O-isopropyl-ethylphosphonodithioic acid and 3.0 parts by weight of triethylamine. Following a procedure similar to that described in Example I, there was obtained 5.87 parts by weight (91% yield) of the title compound, structure confirmed by NMR analysis. The product was a yellow solid with melting point 73°–78° C.

Further examples are listed in Table I as illustrative of the compounds of the present invention. These and other compounds can be prepared in a manner similar to that described in the above examples.

TABLE I

| Compound No. | R | R$^1$ | X | Melting Point (° C) | n$_D^{30}$ |
|---|---|---|---|---|---|
| 1 | OCH$_3$ | OCH$_3$ | S | 76–81 | — |
| 2 | OC$_2$H$_5$ | OC$_2$H$_5$ | S | 103–108 | — |
| 3 | C$_2$H$_5$ | OC$_2$H$_5$ | S | 92–96 | — |
| 4 | C$_2$H$_5$ | OC$_3$H$_7$-iso | S | 73–78 | — |
| 5 | OC$_3$H$_7$-n | OC$_3$H$_7$-n | S | 69–73 | — |
| 6 | C$_2$H$_5$ | OC$_4$H$_9$-iso | S | — | 1.5459 |
| 7 | C$_2$H$_5$ | OCH$_3$ | S | 67–72 | — |

INSECTICIDE EVALUATION

A. Housefly [*Musca domestica* (L.)]

The test compound is diluted in acetone and an aliquot is pipetted onto the bottom of a 55 × 15 mm aluminum dish. To insure even spreading on the bottom of the dish, one ml of acetone containing 0.02% peanut oil is added. After all the solvent has evaporated, the dish is placed in a circular cardboard cage containing 25 one-day-old female houseflies. The cage is covered on the bottom with cellophane and the top with tulle netting, and contains a sugar-water saturated cotton plug for maintenance of the flies. Mortality is recorded after 48 hours. The primary screening level for this test is 100 micrograms of the test compound per 25 female houseflies.

B. Direct Spray Assay on Green Peach Aphid [*Myzus persicae* (Sulzer)]

A radish plant (*Rhaphanus sativus*), approximately 2 cm tall, is transplanted into sandy loam soil in a 3-inch clay pot and infested with 25–50 green peach aphids of mixed ages. Twenty-four hours later the plant is sprayed, to the point of runoff, with a 50—50 acetone-water solution of the test compound. The treated plant is held in the greenhouse and mortality is recorded after 3 days. The primary screening level for this test is 0.05% by weight of the test compound in the acetone-water solution.

C. Systemic Assay on Green Peach Aphid [*Myzus persicae* (Sulzer)]

The test compound is diluted in acetone and an aliquot is thoroughly mixed into 500 grams of dry, sandy loam soil. The treated soil is placed in a pint ice cream carton and a radish plant (*Rhaphanus sativus*) approximately 2 cm tall is transplanted into the carton. The plant is then infested with approximately 25 green peach aphids of mixed ages and placed in the greenhouse. Seven days later mortality is recorded. The primary screening level for this test is 10 ppm by weight of the test compound in the soil.

D. Direct Spray Assay on Black Bean Aphid [*Aphis fabae* (Scop.)]

A nasturtium plant (*Tropaeolum sp.*), approximately 5 cm tall, is transplanted into sandy loam soil in a 3-inch clay pot and infested with 25–50 black bean aphids of mixed ages. Twenty-four hours later the plant is sprayed, to the point of runoff, with a 50—50 acetone-water solution of the test chemical. The treated plant is held in the greenhouse and mortality is recorded after 3 days. The primary screening level for this test is 0.05% by weight of the test compound in the acetone-water solution.

E. Systemic Assay on Black Bean Aphid [*Aphis fabae* (Scop.)]

The test chemical is diluted with acetone and an aliquot is thoroughly mixed into 500 grams of dry, sandy loam soil. The treated soil is placed in a pint ice cream carton and a nasturtium plant (*Tropaeolum sp.*) approximately 5 cm tall is transplanted into the carton. The plant is then infested with approximately 25 black bean aphids of mixed eggs and placed in the greenhouse. Seven days later mortality is recorded. The primary screening level for this test is 10 ppm by weight of the test compound in the soil.

F. German Cockroach [*Blatella germanica* (Linne)]

The test compound is diluted in a 50—50 acetone-water solution. Two milliliters of the solution are sprayed through a DeVilbiss type EGA hand spray gun into a circular cardboard cage containing ten one-month-old German cockroach nymphs. The test cage is covered on the bottom with cellophane and the top with tulle netting. Percent mortality is recorded after 7 days. The primary screening level for this test is 0.1% by weight of the test compound in the acetone-water solution.

G. Southern House Mosquito [*Culex pipiens quinquefasciatus* (Say)]

Insecticidal activity is determined using third-instar larvae of the mosquito (*Culex pipiens quinquefasciatus*). Ten larvae are placed in a six-ounce number 67 Dixie wax paper cup containing 100 milliliters of an aqueous solution of the test chemical. The treated larvae are stored at 70° F, and 48 hours later the mortality is recorded. The primary screening level for this test is 1 ppm by weight of the test compound in the solution.

The primary screening level in each of the above tests was selected for purposes of convenience only, and is not to be understood as representing the highest level at which a viable test for insecticidal activity can be conducted. The insecticidal evaluation proceeded as follows.

For a particular insect, each compound was initially tested at the primary screening level. Those compounds showing greater than 50% kill at this level were then tested at successively lower levels, until the level was found at which approximately 50% kill was achieved. This level is listed as the $LD_{50}$ (50% lethal dose) value in Table II. For those compounds showing approximately 50% kill at the primary screening level, the primary screening level itself is listed as the $LD_{50}$. For those compounds showing less than 50% kill, the number listed is the primary screening level preceded by a ">" (greater than) sign to indicate that a higher level than that reported must be used to achieve 50% kill. Since no tests were run at concentrations higher than the primary screening level, the data as to this latter group is inconclusive with regard to the activity of the compounds of this group at higher concentrations.

Dashes are used in Table II where no tests were performed at all.

TABLE II

Insecticidal Effectiveness - Approximate $LD_{50}$ Values

| Compound No. | HF (μg) | BBA (1) (%) | BBA (2) (ppm) | GPA (1) (%) | GPA (2) (ppm) | GR (%) | MOS (ppm) |
|---|---|---|---|---|---|---|---|
| 1 | >100 | .002 | >10 | >.05 | — | >.1 | >1 |
| 2 | >100 | .0002 | >10 | >.05 | — | >.1 | >1 |
| 3 | 22 | .0002 | >10 | .0005 | 2 | >.1 | >1 |
| 4 | 14 | .0002 | >10 | .001 | 10 | .1 | >1 |
| 5 | >100 | .03 | >10 | — | — | >.1 | >1 |
| 6 | 10 | .0002 | 3 | .0005 | >10 | .008 | .4 |
| 7 | 27 | .001 | >10 | .0002 | 5 | >.1 | >1 |

HF : housefly
BBA : black bean aphid - (1) direct spray, (2) systemic
GPA : green peach aphid - (1) direct spray, (2) systemic
GR : German cockroach
MOS : mosquito
> : "greater than" - indicates compound did not pass primary screen The compounds of this invention are generally used in formulations suitable for convenient application. In general, such formulations will contain inert or occasionally active ingredients or diluent carriers in addition to the active compound. Examples of such ingredients or carriers are organic solvents, such as sesame oil, xylene range solvents, and heavy petroleum; water; emulsifying agents; surface active agents; talc; pyrophyllite; diatomite; gypsum; clays; and propellants, such as dichlorodifluoromethane.

The active compounds can further be combined with dust carriers for application as dusts, with granular carriers for application by fertilizer spreaders or ground or airplane seeders, with wettable powders or flowable carriers for application as water suspensions, or with solvents and surface active materials for application as sprays, aerosols, or emulsions. The compounds or their formulated mixtures can be applied to any habitat of the pests. Examples of such habitats are insect dwellings, clothing, plant surfaces, and soil. If desired, however, the active compositions can be applied directly to organic matter, seeds, or feedstuffs in general, upon which the pests feed, or directly to the pests themselves. When applied in such a manner, it will be advantageous to use a formulation which is not volatile.

The amount of active compound or formulation which is considered to be insecticidally effective is that amount which, when applied to the pest habitat or feedstuff, will kill or substantially injure a significant portion residing or feeding thereon. The active compounds of this invention can be employed either as the sole pesticide component of the formulation or as one of a mixture of compounds in the formulation having similar utility. Furthermore, the presently disclosed pesticide compositions need not be active as such. The purposes of this invention will be fully served by a composition which is rendered active by external influences, such as light, or by physiological action occurring when the preparation is ingested or penetrates into the body of the pest.

The precise manner in which the pesticide compounds of this invention are used in any particular instance will be readily apparent to a person skilled in the art. Generally, the active pesticidal compound will be used as a component of a liquid composition; for example, an emulsion, suspension, or aerosol spray. While the concentration of the active pesticide compound in the present formulation can vary within rather wide limits, ordinarily, the pesticide composition will comprise not more than about 50.0% by weight of the formulation.

What is claimed is:

1. A compound having the formula

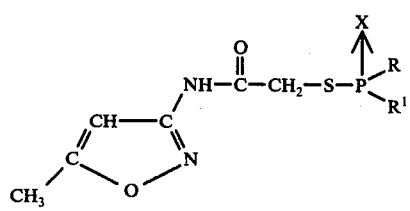

in which
R is alkyl or alkoxy each having 1 to 6 carbon atoms,
$R^1$ is alkoxy having 1 to 6 carbon atoms, and
X is oxygen or sulfur.

2. A compound according to claim 1 in which R is $OCH_3$, $R^1$ is $OCH_3$, and X is S.

3. A compound according to claim 1 in which R is $OC_2H_5$, $R^1$ is $OC_2H_5$, and X is S.

4. A compound according to claim 1 in which R is $C_2H_5$, $R^1$ is $OC_2H_5$, and X is S.

5. A compound according to claim 1 in which R is $C_2H_5$, $R^1$ is $OC_3H_7$-iso, and X is S.

6. A compound according to claim 1 in which R is $OC_3H_7$-n, $R^1$ is $OC_3H_7$-n, and X is S.

7. A compound according to claim 1 in which R is $C_2H_5$, $R^1$ is $OC_4H_9$-iso, and X is S.

8. A compound according to claim 1 in which R is $C_2H_5$, $R^1$ is $OCH_3$, and X is S.

9. A method of controlling insects comprising applying to said insects or the habitat or feedstuff of said insects an insecticidally effective amount of a compound having the formula $$\text{structure: 5-CH}_3\text{-isoxazol-3-yl-NH-C(=O)-CH}_2\text{-S-P(=X)(R)(R}^1\text{)}$$

in which
R is alkyl or alkoxy each having 1 to 6 carbon atoms,
$R^1$ is alkoxy having 1 to 6 carbon atoms, and
X is oxygen or sulfur.

10. A method according to claim 9 in which R is $OCH_3$, $R^1$ is $OCH_3$, and X is S.

11. A method according to claim 9 in which R is $OC_2H_5$, $R^1$ is $OC_2H_5$, and X is S.

12. A method according to claim 9 in which R is $C_2H_5$, $R^1$ is $OC_2H_5$, and X is S.

13. A method according to claim 9 in which R is $C_2H_5$, $R^1$ is $OC_3H_7$-iso, and X is S.

14. A method according to claim 9 in which R is $OC_3H_7$-n, $R^1$ is $OC_3H_7$-n, and X is S.

15. A method according to claim 9 in which R is $C_2H_5$, $R^1$ is $OC_4H_9$-iso, and X is S.

16. A method according to claim 9 in which R is $C_2H_5$, $R^1$ is $OCH_3$, and X is S.

17. An insecticidally effective composition of matter comprising (1) an insecticidally effective amount of a compound having the formula $$\text{structure: 5-CH}_3\text{-isoxazol-3-yl-NH-C(=O)-CH}_2\text{-S-P(=X)(R)(R}^1\text{)}$$

in which
R is alkyl or alkoxy each having 1 to 6 carbon atoms,
$R^1$ is alkoxy having 1 to 6 carbon atoms, and
X is oxygen or sulfur; and (2) an inert diluent carrier.

18. A composition according to claim 17 in which R is $OCH_3$, $R^1$ is $OCH_3$, and X is S.

19. A composition according to claim 17 in which R is $OC_2H_5$, $R^1$ is $OC_2H_5$, and X is S.

20. A composition according to claim 17 in which R is $C_2H_5$, $R^1$ is $OC_2H_5$, and X is S.

21. A composition according to claim 17 in which R is $C_2H_5$, $R^1$ is $OC_3H_7$-iso, and X is S.

22. A composition according to claim 17 in which R is $OC_3H_7$-n, $R^1$ is $OC_3H_7$-n, and X is S.

23. A composition according to claim 17 in which R is $C_2H_5$, $R^1$ is $OC_4H_9$-iso, and X is S.

24. A composition according to claim 17 in which R is $C_2H_5$, $R^1$ is $OCH_3$, and X is S.

* * * * *